United States Patent
Hartmann-Bax et al.

(10) Patent No.: US 11,116,987 B2
(45) Date of Patent: Sep. 14, 2021

(54) ELECTRICAL CONTACT COMPONENT

(71) Applicant: BIOTRONIK SE & Co. KG, Berlin (DE)

(72) Inventors: Kathy Hartmann-Bax, Nuthe-Urstromtal (DE); Ruien Wali, Berlin (DE)

(73) Assignee: BIOTRONIK SE & CO. KG

( * ) Notice: Subject to any disclaimer, the term of this patent is extended or adjusted under 35 U.S.C. 154(b) by 8 days.

(21) Appl. No.: 16/839,246

(22) Filed: Apr. 3, 2020

(65) Prior Publication Data

US 2020/0330772 A1 Oct. 22, 2020

(30) Foreign Application Priority Data

Apr. 17, 2019 (EP) .................... 19169882
Jun. 17, 2019 (EP) .................... 19180525

(51) Int. Cl.
*A61N 1/375* (2006.01)
*H01R 13/11* (2006.01)
*H01R 13/24* (2006.01)
*H01R 13/502* (2006.01)

(52) U.S. Cl.
CPC .......... *A61N 1/3752* (2013.01); *H01R 13/111* (2013.01); *H01R 13/2421* (2013.01); *H01R 13/2478* (2013.01); *H01R 13/2492* (2013.01); *H01R 13/502* (2013.01); *H01R 2201/12* (2013.01)

(58) Field of Classification Search
CPC ............... A61N 1/3752; H01R 13/111; H01R 13/2421; H01R 13/2478; H01R 13/2492
USPC .................................... 17/17, 669
See application file for complete search history.

(56) References Cited

U.S. PATENT DOCUMENTS

| | | | | |
|---|---|---|---|---|
| 1,450,172 A * | 4/1923 | Dewald, Sr. | ......... | H01R 39/643 439/17 |
| 2,328,212 A * | 8/1943 | Heiner | .................... | H01R 39/00 439/17 |
| 3,387,250 A * | 6/1968 | Bjorn | ................... | H01R 39/643 439/17 |
| 3,766,512 A * | 10/1973 | Falbet | .................... | H01R 24/58 439/101 |
| 3,832,674 A * | 8/1974 | Florian | ................ | H01R 13/523 439/281 |

(Continued)

FOREIGN PATENT DOCUMENTS

DE    10 2016 217 673 A1    3/2018

OTHER PUBLICATIONS

International Search Report, Application No. 19180525.B-1124, dated Dec. 19, 2019.

*Primary Examiner* — Neil Abrams
(74) *Attorney, Agent, or Firm* — Craig A. Fieschko, Esq.; Dewitt LLP (57) ABSTRACT

An electrical contact component for a contact socket of an implantable medical device includes an electrical contact element for electrically contacting an electrical counter contact (such as an electrode plug), and an electrically conductive outer ring having a plug borehole for receiving the electrical counter contact. The interior of the outer ring includes a depression receiving the electrical contact element. The electrical contact element is formed by contact bodies (such as balls or rolls), a cage element for receiving the contact bodies, and at least one electrically conductive spring element.

20 Claims, 6 Drawing Sheets

(56) References Cited

U.S. PATENT DOCUMENTS

| | | | | |
|---|---|---|---|---|
| 3,848,223 | A * | 11/1974 | Pechard | H01R 12/721 |
| | | | | 439/637 |
| 4,157,857 | A * | 6/1979 | Sabo | H01R 12/721 |
| | | | | 439/637 |
| 4,469,104 | A * | 9/1984 | Peers-Trevarton | |
| | | | | A61N 1/3752 |
| | | | | 607/27 |
| 4,911,644 | A * | 3/1990 | Bond | H01R 12/62 |
| | | | | 439/493 |
| 5,281,148 | A * | 1/1994 | Thompson | H01R 12/714 |
| | | | | 439/17 |
| 5,321,583 | A * | 6/1994 | McMahon | H01R 13/2414 |
| | | | | 174/255 |
| 6,162,062 | A * | 12/2000 | Liao | H01R 39/10 |
| | | | | 439/17 |
| 6,498,952 | B2 | 12/2002 | Imani et al. | |
| 9,138,586 | B2 * | 9/2015 | Eiger | A61N 1/3752 |
| 9,225,114 | B2 * | 12/2015 | Sinclair | H01R 13/6276 |
| 10,833,440 | B2 * | 11/2020 | Beck | H01R 13/113 |
| 2003/0232533 | A1 * | 12/2003 | Burmeister | H01R 13/02 |
| | | | | 439/259 |
| 2013/0197603 | A1 | 8/2013 | Eiger | |
| 2016/0164195 | A1 * | 6/2016 | Starke | H01R 13/187 |
| | | | | 439/816 |
| 2018/0183179 | A1 * | 6/2018 | Byrd | A61M 25/0136 |
| 2019/0214779 | A1 * | 7/2019 | Beck | H01R 24/58 |
| 2020/0330772 | A1 * | 10/2020 | Hartmann-Bax | H01R 13/2492 |

* cited by examiner

ELECTRICAL CONTACT COMPONENT

FIELD OF THE INVENTION

The present invention relates to an electrical contact component for a medical implant.

BACKGROUND OF THE INVENTION

Medical implants, in particular active medical implants, typically have therapeutic and/or diagnostic electrodes which receive or deliver electrical impulses in the target tissue. To ensure the implant's functionality, it is necessary to establish a safe and reliable electrical contact between the electrode(s) and the components inside the implant, and in particular the energy source and the control circuits.

International standards exist for electrode contacts, such as DF-4/IS-4 for 4-pole plug connections or connectors. One variant for implementing the IS4 standard in active implants (IPG/ICD) provides an electrical contact component having a rotationally symmetrical spring sleeve and a spring element welded into the spring sleeve. A preferred spring element is, for example, a canted coil spring, which is fused together to form an annular spring or toroidal spring. However, this variant is complex to produce and assemble, in particular the manufacture of the annular or toroidal spring, and production is difficult to automate.

SUMMARY OF THE INVENTION

The invention seeks to provide an electrical contact component for a contact socket (plug receptacle) of an implantable medical device, which enables robust and reliable electrical contacting and is comparatively easy to produce. A preferred electrical contact component includes an electrical contact element for electrically contacting an electrical counter contact (e.g., the plug of an electrode to be electrically connected to an implantable medical device), and an electrically conductive outer ring having a plug borehole for receiving the electrical counter contact, wherein the interior of the outer ring includes a depression (e.g., a groove) for receiving the electrical contact element.

The electrical contact element is preferably formed by several electrically conductive contact bodies, and at least one cage element for receiving the electrically conductive contact bodies. As used in this document, the term "contact bodies" refers to any body configured to be able to electrically contact the mating electrical counter contact. The term "cage element" refers to any structure configured to receive the electrically conductive contact bodies, and keep the contact bodies in spaced positions with respect to one another.

The electrically conductive contact bodies are preferably configured as balls or rolls (cylindrical sections), with the cage element(s) being accordingly configured as a roll cage or a ball cage. The depression is configured to position and guide the electrical contact element (the cage element(s) and electrically conductive contact bodies). The cage element(s) is/are preferably situated within the groove or other depression. The cage element can include multiple openings for the electrically conductive contact bodies, wherein the electrically conductive contact bodies extend through the cage element so that the electrically conductive contact bodies may electrically contact the electrical counter contact. The openings may have a smaller diameter than the diameter of the contact bodies arranged therein. The contact bodies are thereby restrained by the cage element within the depression. The cage element is preferably configured as an annular ribbon (e.g., a sheet metal ribbon) which includes openings for receiving the contact bodies, with the diameters of the openings being smaller than the diameters of the contact bodies. The cage element and/or the openings thereof are preferably configured such that the contact bodies have a predefined degree of freedom of movement, that is, the contact bodies are able to move within their openings. Preferably, the electrical contact element includes 7 to 15 contact bodies.

The electrical contact component preferably further includes a spring element within the depression, and between the contact bodies and the inside of the outer ring, wherein the spring element is configured to keep at least one of the contact bodies in electrical contact with the outer ring and the electrical counter contact at all times, so that a permanent electrical contact is provided between the electrical counter contact and the outer ring. If the cage element itself is electrically conductive, the spring element may be configured to keep one of the contact bodies and the outer ring in electrical contact, and another of the contact bodies and the electrical counter contact in electrical contact, so as to ensure a permanent electrical contact between the electrical counter contact and the outer ring. The spring element may assume any configuration, location, or orientation within the depression, provided that at least one of the contact bodies and the outer ring, and at least one of the contact bodies and the electrical counter contact, are kept in permanent electrical contact. The spring element exerts a force onto the contact body/bodies that is directed toward the electrical counter contact.

In a preferred version, the outer ring includes a housing and a cover, wherein the housing and the cover each include an interior web, and the webs, together with the interior of the housing, form the groove or other depression for receiving the electrically conductive contact element. The groove or other depression preferably has or approximates one of the following cross-sectional shapes: semi-circular (including parabolic), triangular (i.e. having two opposing planar sidewalls joined at a vertex), rectangular (i.e., having two opposing parallel planar sidewalls connected by a planar floor), trapezoidal (i.e., having a planar floor with diverging planar sidewalls), or quarter-round (i.e., having opposing sidewalls which bulge into the depression). The housing may be integrally joined to the cover, as by pressing, adhesive bonding, soldering, riveting, spot-welding or welding.

The spring element is preferably configured as an annular spring element, particularly as a closed annular spring element (i.e., as a closed loop). The annular spring element preferably has one of the following cross-sectional shapes: round (annular tube), semi-circular, s-shaped, z-shaped, c-shaped, rectangular, or omega-shaped. The annular spring element may simply be configured as a coil spring.

In another version of the electrical contact component, a spring element is arranged on each contact body of the electrical contact component, wherein each spring element is situated between its respective contact body and the inside of the outer ring. Each contact body may be integrally joined to its respective spring element.

The spring element and its contact body may be configured as a spring-loaded pressure piece. Such a spring-loaded pressure piece may be formed by a sleeve wherein the spring element, and preferably its contact body, is situated. The spring-loaded pressure piece may therefore define a spring-loaded contact body (e.g., a ball). The sleeve may also serve as an individual cage element in the process, whereby a cage element for all electrically conductive contact bodies can be dispensed with.

The cage element may have a flexibly resilient (spring-elastic) design. This version of the invention advantageously need not have an additional spring element, since such a cage element may keep the contact bodies in electrical contact with the inside of the outer ring and the electrical counter contact. Here, the cage element is preferably configured as an electrically conductive sheet metal cage.

The electrically conductive outer ring and the cage element(s) are preferably made of a metal or a metal alloy. The outer ring and the cage element may thus advantageously be more easily welded, soldered, or otherwise joined. At the same time, the cage element may also help to establish a reliable electrical contact between the outer ring and the electrical counter contact. The electrically conductive outer ring and the cage element(s) are preferably integrally joined (i.e., formed in once piece), in particular by pressing, adhesive bonding, soldering, riveting, spot-welding or welding.

The cage element is preferably formed of at least one of the following materials: plastic, in particular a thermoset material, a thermoplastic material, an elastomer or a combination thereof, stainless steel, in particular chromium-nickel-molybdenum steel, such as 1.4435, a platinum-iridium alloy, a nickel-cobalt alloy, in particular MP35N, titanium or a titanium alloy, in particular Nitinol. The outer ring is preferably formed (at least substantially) of stainless steel, in particular chromium-nickel-molybdenum steel, such as 1.4435, a platinum-iridium alloy, a nickel-cobalt alloy, in particular MP35N, titanium or a titanium alloy. The contact bodies are preferably formed (at least substantially) of stainless steel, in particular chromium-nickel-molybdenum steel, such as 1.4435, a nickel-cobalt alloy, in particular MP35N, titanium or a titanium alloy.

The electrical contact component is preferably provided within a contact socket (plug receptacle) for an implantable medical device such as a cardiac pacemaker, a cardioverter-defibrillator, or a neurostimulator, wherein the contact socket may receive (and communicate electrical signals with) an electrical counter contact such as the plug of an electrode lead. Such an implantable medical device typically includes a hermetically sealed housing including an electrical feedthrough leading to necessary components, such as the implant's energy source, control electronics, diagnostic electronics, and/or its capacitor, arranged within the housing. Such a contact socket is typically an integral part of any header of the implantable medical device, wherein the contact socket, and in particular the contact component, is in electrical communication with the feedthrough (and thus the aforementioned components) within the housing of the implantable medical device via a ribbon conductor or other electrical conductor. The electrical contact component of the contact socket is then in electrical contact with the feedthrough (and thus the aforementioned components) of the implantable medical device. The contact socket can also be provided in the housing of an implantable medical device which does not have a header, in which case the electrical contact component may be electrically connected with the components of the implantable medical device without a hermetic electric feedthrough. The contact socket preferably includes 1 to 10, and in particular 4 to 8, of the electrical contact components.

BRIEF DESCRIPTION OF THE DRAWINGS

Exemplary versions of the invention are described below with reference to the accompanying drawings, wherein:

FIGS. 1A-1F (collectively referred to as FIG. 1) show an electrical contact component exemplifying the invention, with FIG. 1A providing an exploded/disassembled cross-sectional view, FIG. 1B providing an assembled cross-sectional view, FIG. 1C providing an assembled full view, FIG. 1D showing an exemplary contact socket (plug receptacle) having several of the electrical contact component, and FIG. 1E showing the electrical contact component with an electrode received therein;

DETAILED DESCRIPTION OF EXEMPLARY VERSIONS OF THE INVENTION

An electrical counter contact is required in the header of an IPG or ICD for contacting an IS4 or DF4 electrode. Preferred versions of the invention use a rolling bearing, in particular a ball bearing, as the electrical contact, instead of the conventional spring contacts.

As shown in FIG. 1, an exemplary electrical contact component 100 includes an outer profile ring 110 having a depression (groove) 111 on its interior, a spring ring 150, several (e.g., seven to fifteen) contact bodies 142 (here provided by balls), and a multi-piece cage 141 for receiving the balls 142.

The outer profile ring 110 is configured such that the contact bodies (balls) 142 provide at least one electrical punctiform contact, and preferably multiple punctiform contacts, with the profile ring 110. The groove 111 of the profile ring 110 can have different shapes (round, semi-circular, rectangular, trapezoidal, prism, etc.). A wiring strip or ribbon, which communicates energy/power, may be welded or otherwise electrically affixed onto the outside of the profile ring 110. The profile ring 110 is preferably a traditional turned part, but may also be produced by metal injection molding (MIM) or other shaping methods, such as printing or compressing and sintering. The profile ring 110 may be designed in one piece, but may also have a multi-piece design, as exemplified by profile ring segments 120 (housing) and 130 (cover). If a multi-piece profile ring 110 is used, its segments 120/130 are preferably integrally joined to one another, for example by compression, welding, adhesive bonding, soldering, riveting or spot-welding, after installation of the contact bodies 142 and the cage 141.

Figure 1A:
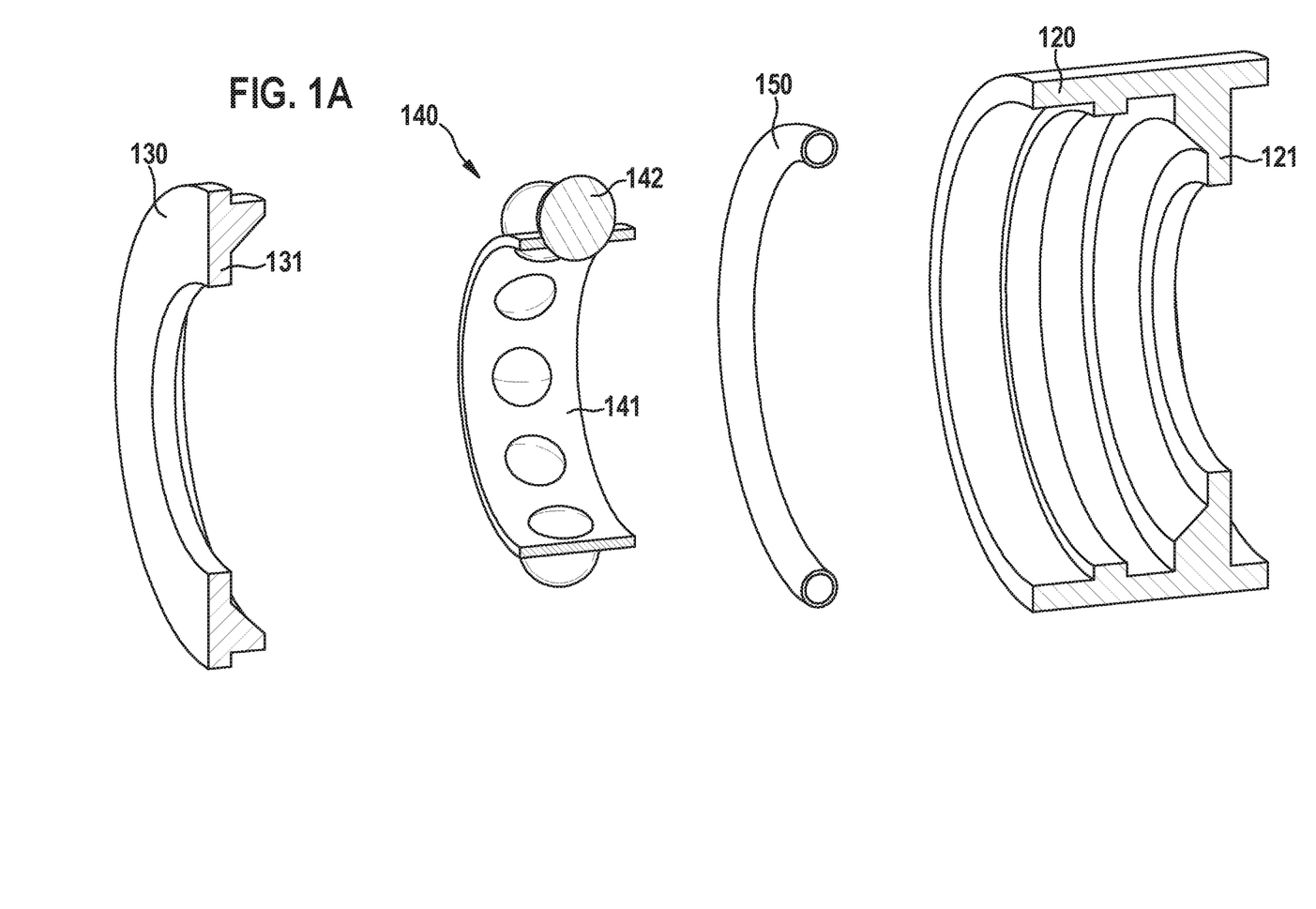
Figure 1B:
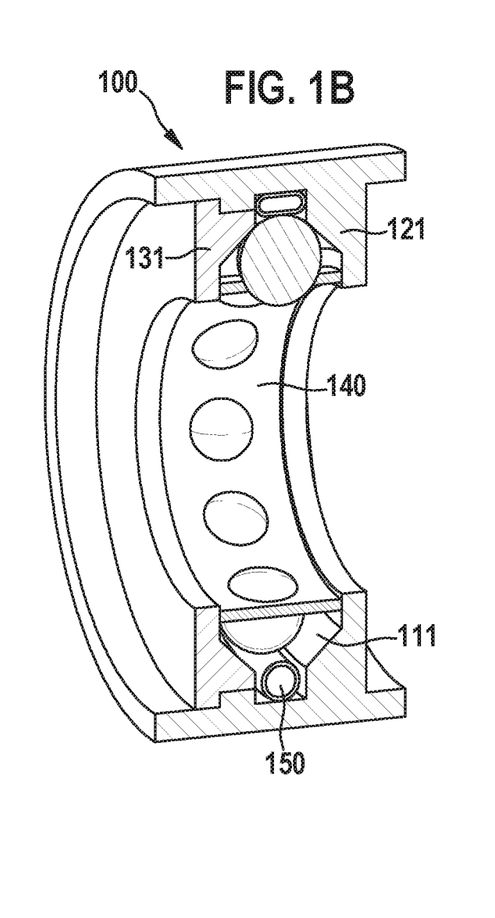
Figure 1C:
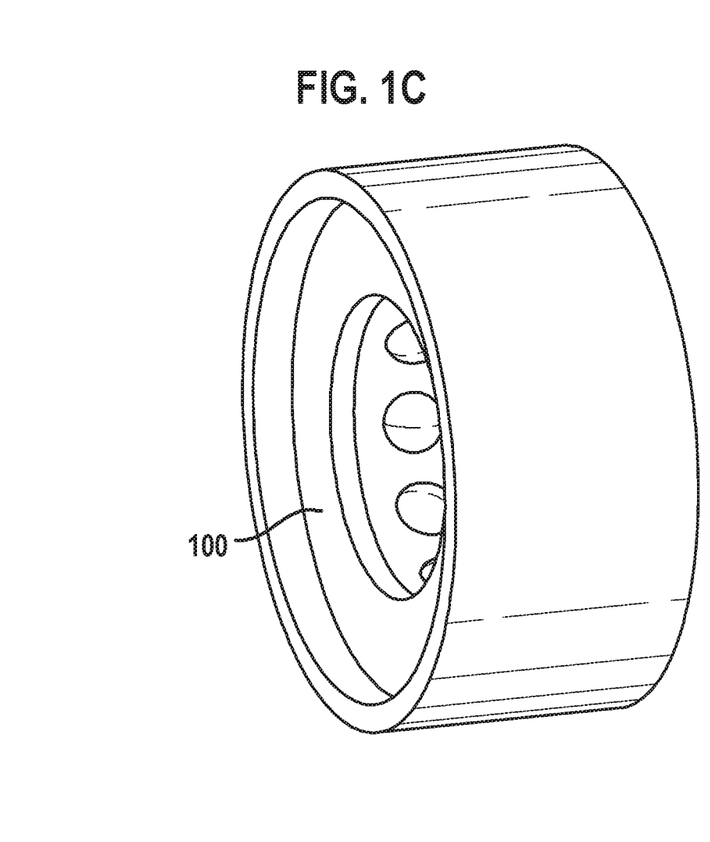
Figure 1D:
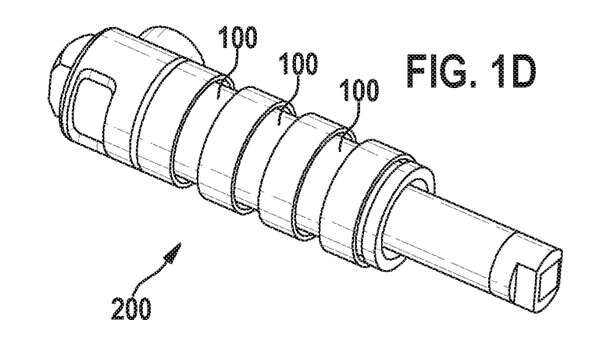
Figure 1E:
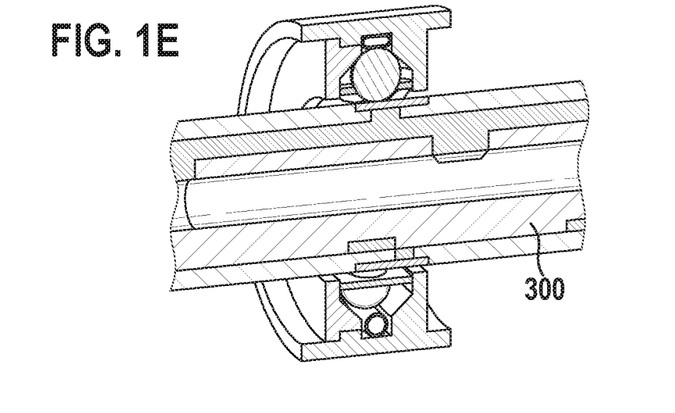
Figure 2:
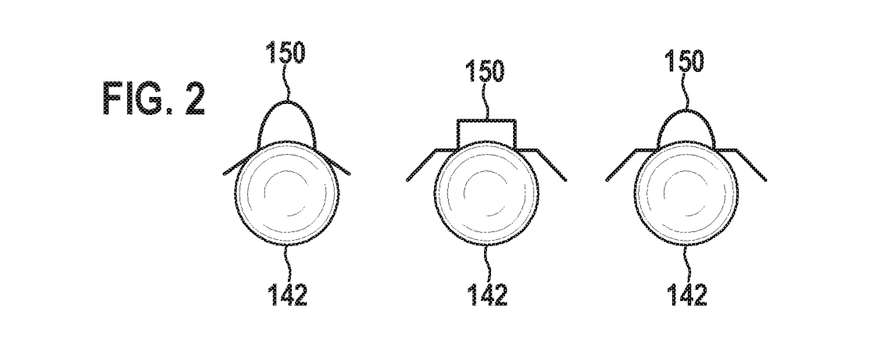
FIG. 2 shows exemplary shapes of the depression (groove) of the outer profile ring (or of the spring element within the depression)
Figure 3:
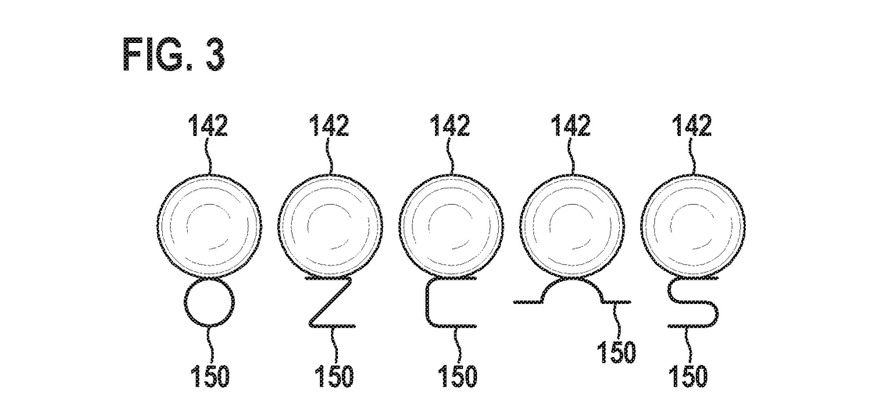
FIG. 3 shows further exemplary shapes of the spring element.

The spring ring 150 is preferably a one-piece spring-loaded (elastically compressible and extendable) component which ensures permanent contact between the contact bodies (balls) 142 and the profile ring 110 on the one hand, and allows the contact bodies 142 to spring in the radial direction (to the inside and outside) on the other hand. Referring to FIGS. 2 and 3, the spring ring 150 may have an open or a closed configuration, and may have cross-sectional shapes with o-shaped, z-shaped, c-shaped, s-shaped, or other geometries. The spring ring 150 may alternatively be a coil spring loop.

The contact bodies (balls) 142 are dimensioned so that an electrical contact is realized between the electrode 300 (FIG. 1E) and the profile ring 110 by way of the spring ring 150 when the electrode 300 is inserted.

The cage 141 is used to retain the contact bodies (balls) 142 in the profile ring 110, holding the contact bodies 142 in spaced relationship. The cage 141 may be resiliently flexible in at least the radial direction for the case where the spring ring 150 can be omitted as an element. The cage 141 may be designed as a closed or an open ring, and can be formed of one or multiple parts.

Suitable materials for the cage 141 are, for example, plastic (such as polyamide), Nitinol, 1.4435, platinum iridium, MP35N, titanium, or stainless steel. The outer ring 110 is preferably made of a platinum iridium alloy, and the contact bodies 142 of the ball bearing are preferably made of MP35N, 1.4435 (stainless steel), or titanium. However, any materials that meet the requirements with regard to an electrical contact in a permanent implant may be used.

Figure 4A:
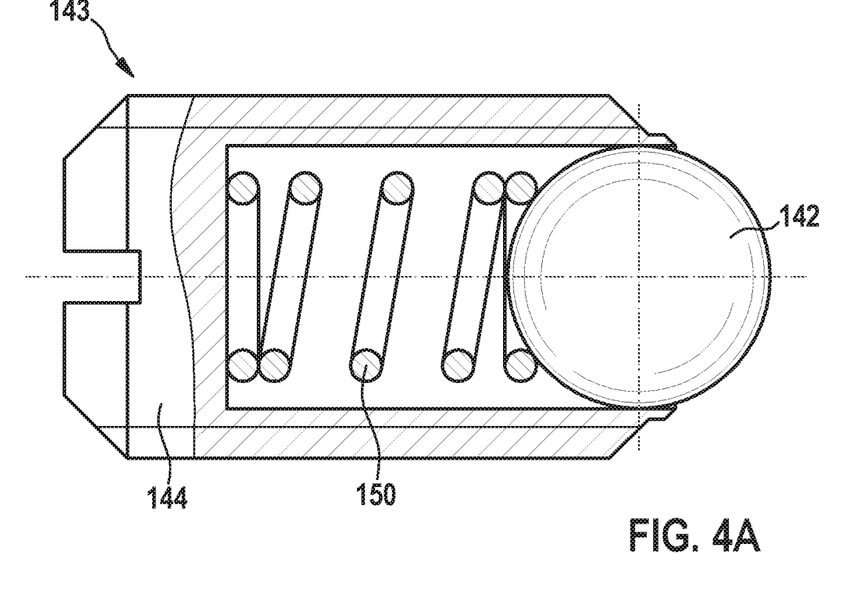
FIGS. 4A-D (collectively referred to as FIG. 4) show alternative versions of elements of the electrical contact component.
Figure 4B:
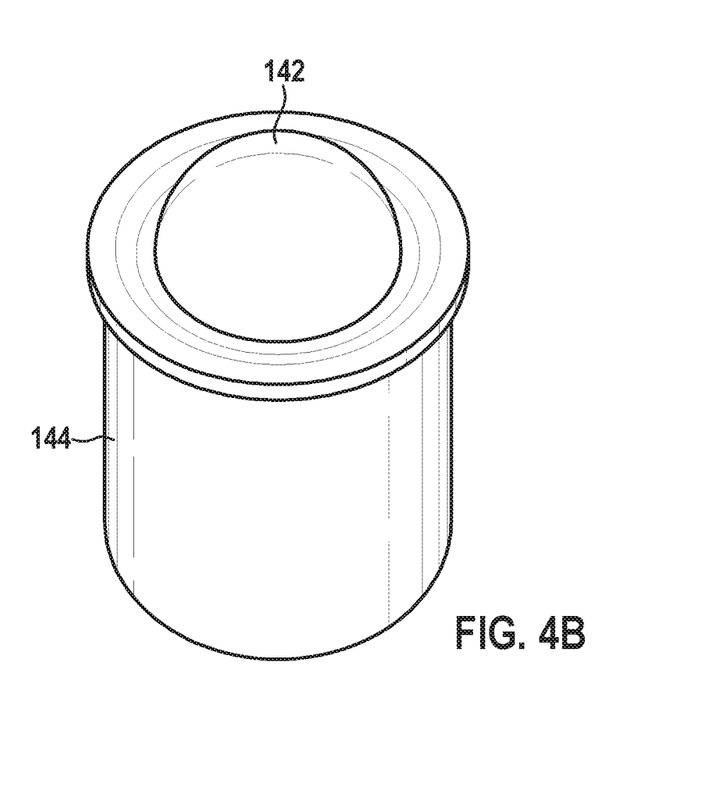
Figure 4C:
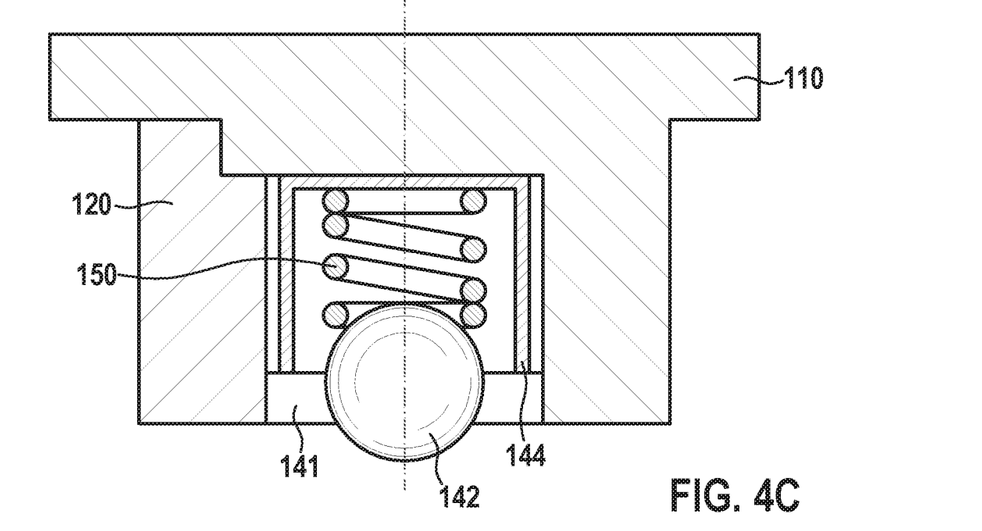
Figure 4D:
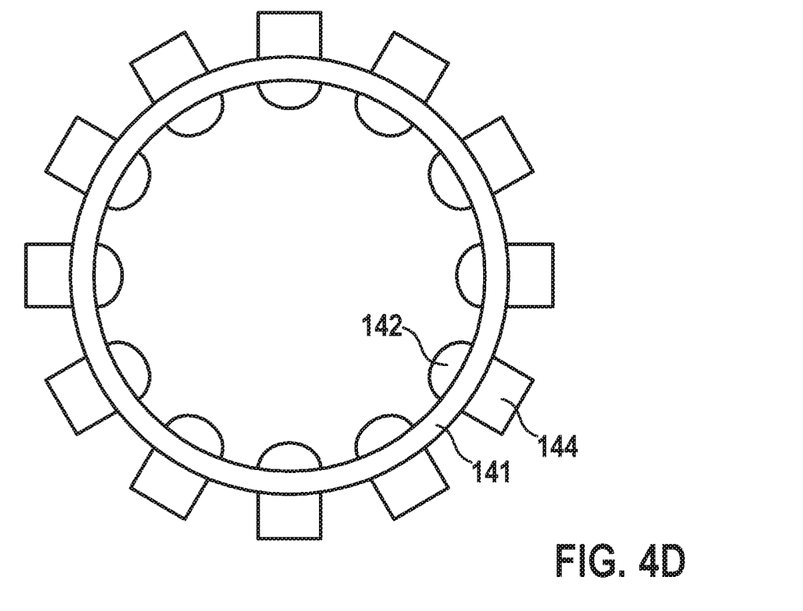

FIGS. 4A to 4D show another exemplary version of the electrical contact element. Here a respective individual spring element 150 is provided for each contact body 142 (each contact body 142 preferably being designed as a ball). The spring element 150 is situated within a sleeve 144 which forms a spring-loaded pressure piece 143 (FIGS. 4A and 4B). The spring element 150 is preferably designed as a helical spring. As is shown in FIG. 4C, the spring-loaded pressure piece 143, and in particular the sleeve 144 and the spring element 150, are situated in the groove 111 (FIG. 1B) of the outer profile ring 110, composed of the housing 120 and the cover 130. In this version as well, a cage element 141 is used to space apart and position the contact bodies 141, and thus also the spring elements 150 (FIGS. 4C and 4D).

The versions of the invention described above are merely exemplary, and the invention is not intended to be limited to these versions. Rather, the scope of rights to the invention is limited only by the claims set out below, and the invention encompasses all different versions that fall literally or equivalently within the scope of these claims.

What is claimed is:

1. An electrical contact component (100) for a contact socket (200) of an implantable medical device, the electrical contact component including:
   A. an electrical contact element (140) configured to electrically contact an electrical counter contact (300); and
   B. an electrically conductive outer ring (110) having a borehole configured to receive the electrical counter contact (300), the outer ring (110) having an interior including a depression (111) receiving the electrical contact element (140),
   wherein the electrical contact element (140) includes:
   a. several contact bodies (142),
   b. a cage element (141) receiving the contact bodies (142), and
   c. an electrically conductive spring element (150):
      (1) situated within the depression (111) between the contact bodies (142) and the interior of the outer ring (110), and
      (2) being configured to keep at least one of the contact bodies (142) in electrical contact with the outer ring (110) and the electrical counter contact (300).

2. The electrical contact component (100) of claim 1 wherein:
   a. the outer ring (110) includes a housing (120) and a cover (130),
   b. the housing (120) and the cover (130) each including an interior having a web (121, 131) thereon,
   c. the webs (121, 131) bound the depression (111).

3. The electrical contact component (100) of claim 1 wherein the depression (111) has one of the following cross-sectional shapes: semi-circular, triangular, rectangular, trapezoidal, or quarter-round.

4. The electrical contact component (100) of claim 1 wherein the contact bodies (142) have circular cross-sectional shapes.

5. The electrical contact component (100) of claim 4 wherein the contact bodies (142) are defined by balls or rolls.

6. The electrical contact component (100) of claim 1 wherein:
   a. the depression (111) is defined by an annular groove within the interior of the outer ring (110), and
   b. the cage element (141) and the electrically conductive spring element (150) extend through at least substantially the entirety of the depression.

7. The electrical contact component (100) of claim 1 wherein one or more of:
   a. the depression (111),
   b. the cage element (141)), and
   c. the spring element (150),
   extend about at least substantially the entirety of the borehole.

8. The electrical contact component (100) of claim 1 wherein the spring element (150) is defined by a resiliently flexible member extending through at least substantially the entirety of the depression (111).

9. The electrical contact component (100) of claim 1 wherein the spring element (150) is defined by an annulus.

10. The electrical contact component (100) of claim 9 wherein the annulus is an annular tube.

11. The electrical contact component (100) of claim 9 wherein the annulus is an annular coil spring.

12. The electrical contact component (100) of claim 9 wherein the annular spring element (150) has one of the following cross-sectional shapes: round, z-shaped, c-shaped, semi-circular, Ω-shaped, or rectangular.

13. The electrical contact component (100) of claim 1 wherein each contact body (142) has a respective spring element (150) urging against each contact body (142).

14. The electrical contact component (100) of claim 1 wherein:
   a. the cage element (141) includes an annular ring having openings therein,
   b. each contact body (142) is received within one of the openings,
   c. each opening is sized to prevent passage of its contact body (142) therethrough.

15. The electrical contact component (100) of claim 1 wherein the electrical contact element (100) includes 7 to 15 contact bodies (142).

16. The electrical contact component (100) of claim 1 further including an implantable medical device wherein the electrical contact component (100) is situated.

17. The implantable medical device of claim 16 wherein the implantable medical device defines a cardiac pacemaker, a cardioverter-defibrillator, or a neurostimulator.

18. An electrical contact component (100) for a contact socket (200) of an implantable medical device, the electrical contact component including:
   A. an electrically conductive outer ring (110) having a borehole configured to receive an electrical counter contact (300), the outer ring (110) having an interior with a depression (111) defined therein, B. an electrical contact element (140):
   a. configured to electrically contact an electrical counter contact (300) received within the borehole of the outer ring (110),
   b. situated within the depression (111), and
   c. including:
     (1) a cage element (141),
     (2) contact bodies (142) situated within openings in the cage element (141),
     (3) an electrically conductive spring element (150) situated in compression between the contact bodies (142) and the interior of the outer ring (110).

19. The electrical contact component (100) of claim 18 wherein:
   a. the depression (111) is defined by an annular groove within the interior of the outer ring (110),
   b. the cage element (141) and the electrically conductive spring element (150) extend through at least substantially the entirety of the depression, and
   c. the contact bodies (142) are defined by balls or rolls.

20. An electrical contact component (100) for a contact socket (200) of an implantable medical device, the electrical contact component including:

A. an electrically conductive outer ring (110) having a borehole configured to receive an electrical counter contact (300), the outer ring (110) having an interior with an annular depression (111) defined therein, B. an electrical contact element (140):
   a. configured to electrically contact an electrical counter contact (300) received within the borehole of the outer ring (110),
   b. including:
     (1) an electrically conductive spring element (150) extending along the depression (111) against the outer ring (110),
     (2) an annular cage element (141) situated radially inwardly from the spring element (150), the cage element (141) having spaced openings thereon, and
     (3) contact bodies (142) situated between the spring element (150) and the cage element (141) and within the openings.

\* \* \* \* \*